United States Patent [19]

Michael

[11] Patent Number: 4,961,871

[45] Date of Patent: Oct. 9, 1990

[54] POWDERED ABRASIVE CLEANSERS WITH ENCAPSULATED PERFUME

[75] Inventor: Daniel W. Michael, Cincinnati, Ohio

[73] Assignee: The Procter & Gamble Company, Cincinnati, Ohio

[21] Appl. No.: 436,274

[22] Filed: Nov. 14, 1989

[51] Int. Cl.⁵ ........................ C11D 3/50; C11D 17/00; A61K 7/46

[52] U.S. Cl. ........................ 252/174.11; 252/174.13; 252/174.25; 252/135; 252/174.17; 252/174.18; 252/90; 512/4

[58] Field of Search ............... 252/8.6, 174.11, 174.13, 252/174.25; 8/526, 137; 512/4

[56] References Cited

U.S. PATENT DOCUMENTS

| | | | |
|---|---|---|---|
| 2,800,457 | 7/1957 | Green et al. | 252/316 |
| 2,800,458 | 7/1957 | Green | 252/316 |
| 3,041,289 | 6/1962 | Katchen et al. | 252/316 |
| 3,201,353 | 8/1965 | Corben | 252/316 |
| 3,244,640 | 4/1966 | Studt et al. | 252/316 |
| 3,317,433 | 5/1967 | Eichel | 252/316 |
| 3,436,355 | 4/1969 | Bakan | 427/213.33 |
| 3,533,958 | 10/1970 | Yurkowitz | 252/316 |
| 3,697,437 | 10/1972 | Fogle et al. | 252/316 |
| 3,888,689 | 6/1975 | Maekawa et al. | 106/24 |
| 4,010,038 | 3/1977 | Iwasaki et al. | 106/22 |
| 4,145,184 | 3/1979 | Brain et al. | 8/137 |
| 4,234,627 | 11/1980 | Schilling | 427/242 |
| 4,446,032 | 5/1984 | Munteanu et al. | 252/8.6 |

FOREIGN PATENT DOCUMENTS 1367622 9/1974 United Kingdom .

*Primary Examiner*—Paul Lieberman
*Assistant Examiner*—J. Darland
*Attorney, Agent, or Firm*—Robert B. Aylor; Richard C. White

[57] ABSTRACT

Powdered, abrasive, hard surface cleansers containing micro-encapsulated perfume wherein the capsules are essentially water-insoluble, but can become perfume permeable during use by the combined action of water and abrasive. The preferred capsules are formed from gelatin and a polyanionic material by coacervation techniques and then are cross-linked to provide controlled water insolubility.

8 Claims, No Drawings

POWDERED ABRASIVE CLEANSERS WITH ENCAPSULATED PERFUME

BACKGROUND OF THE INVENTION

1. Field of the Invention

This invention relates to powdered abrasive cleansers comprising synthetic surfactants, abrasives and encapsulated perfume.

2. Background Art

Powdered abrasive cleansers have long been known to be useful for scouring porcelain sinks and fixtures, hard metallic materials, pots and pans, and similar surfaces which require high levels of mechanical abrasive for cleaning. The formulation of such powdered abrasive cleansers is discussed in great detail in U.S. Pat. Nos. 3,583,922, McClain et al., issued June 8, 1971; 3,829,385, Abbott, Jr., et al., issued Aug. 13, 1974; 3,715,314, Morganstern, issued Feb. 6, 1973; and U.S. Pat. No. 4,287,080, Siklosi, issued Sept. 1, 1981, all of said patents being incorporated herein by reference.

Microencapsulation of various hydrophobic liquids is well known. Microcapsules have been suggested for encapsulation of perfumes, medicines, adhesives, dyestuffs, inks, etc. It has specifically been suggested to microencapsulate fragrances for use in liquid or solid fabric softeners. See, e.g., U.S. Pat. No. 4,446,032, Munteanu et al., issued May 1, 1984, incorporated herein by reference. The individual perfume and/or flavor compounds which can be encapsulated are also well known, having been disclosed in, e.g., U.S. Pat. No. 3,971,852, Brenner et al., issued July 27, 1976; U.S. Pat. No. 4,515,705, Moeddel, issued May 7, 1985; U.S. Pat. No. 4,741,856, Taylor et al., issued May 3,1988, etc., all of the above patents being incorporated herein by reference.

Microencapsulation techniques, including so-called "coacervation" techniques, are also well known, having been described, for example, in U.S. Pat. No. 2,800,458, Green, issued July 23, 957; U.S. Pat. No. 3,159,585, Evans et al., issued Dec 1, 1964; U.S. Pat. No. 3,533,958, Yurkowitz, issued Oct. 13, 1970; U.S. Pat. No. 3,697,437, Fogle et al., issued Oct. 10, 1972; U.S. Pat. No. 3,888,689, Maekawa et al., issued June 10, 1975; Brit. Pat. 1,483,542, published Aug. 24, 1977; U.S. Pat. No. 3,996,156, Matsukawa et al., issued Dec. 7, 1976; U.S. Pat. No. 3,965,033, Matsukawa et al., issued June 22, 1976; and U.S. Pat. No. 4,010,038, Iwasaki et al., issued Mar. 1. 1977, etc., all of said patents being incorporated herein by reference.

Other techniques and materials for forming microcapsules are disclosed in U.S. Pat. No. 4,016,098, Saeki et al., issued Apr. 5, 1977; U.S. Pat. No. 4,269,729, Maruyama et al., issued May 26, 1981; U.S. Pat. No. 4,303,548, Shimazaki et al., issued Dec. 1, 1981; U.S. Pat. No. 4,460,722, Igarashi et al., issued July 17, 1984; and U.S. Pat. No. 4,610,927, Igarashi et al., issued Sept. 9, 1986, all of said patents being incorporated herein by reference.

For certain utilities such as that disclosed in U.S. Pat. No. 4,446,032, supra, it is desirable to have a strong capsule wall to permit preparation of finished compositions that contain microcapsules utilizing processes that tend to destroy capsule walls and yet have the capsules readily activated in some way during use. Heretofore, it has been thought that the capsule walls should be water-soluble, as disclosed in British Pat. No. 1,367,622, Bradbury et al., incorporated herein by reference. The '622 British patent teaches that there is an essential balance between strength and water solubility required and that the degree of cross-linking should be low. 1% and 1.5% of glutaraldehyde cross-linking agent were preferred over 2%. Water-insoluble capsules are implicitly considered to be ineffective.

SUMMARY OF THE INVENTION

A powdered abrasive cleanser comprising:

(a) from about 0.1% to about 10% of surfactant;

(b) from about 10% to about 95% of water-insoluble abrasive material;

(c) from 0% to about 80% detergency builder; and (d) from about 0.02% to about 5% perfume, microencapsulated in an essentially water-insoluble material.

"Water-insoluble" as used herein means the encapsulating wall material will retain its basic structural integrity when placed in water without appreciable mechanical action being applied. The wall material can, and preferably will, be weakened by the action of wetting and will preferably become partially permeable. However, significant release only occurs when abrasive mechanical action is applied.

This invention relates to powdered abrasive cleanser compositions comprising microcapsules containing hydrophobic perfume liquid cores. Such microcapsules comprise a relatively large central core of hydrophobic liquid perfume material, e.g., cores having diameters in excess of about 50 microns. Preferably, the microcapsules have complex structures in which the capsule walls surrounding the central cores comprise substantial amounts of relatively small wall inclusion particles of core material and/or other materials, so that mechanical action can readily disrupt the wall, said small wall inclusion particles having particle sizes of less than about 15 microns, preferably less than about 10 microns, more preferably less than about 5 microns.

Microcapsules made by coacervation processes from gelatin and a polyanionic material, and especially such microcapsules having a complex structure, are particularly desirable for use in powdered abrasive cleanser compositions.

Microcapsules having this complex wall structure can be made by coacervation processes in which at least a major portion of the material to be encapsulated is converted to an emulsion having particle diameters of at least about 50 microns and another smaller portion of the same material, or a different material, or mixtures thereof, is converted to an emulsion or suspension having particle diameters of less than about 15 microns before encapsulation, e.g., the coacervation process uses an emulsion with a bimodal distribution.

During a typical coacervation process for forming microcapsules, smaller hydrophobic emulsion wall inclusion particles will be encapsulated first and they in turn will coalesce around the larger emulsion core particles to form walls. All, or a portion of the small wall inclusion particles can be a different material than the central core material, preferably a material that can be solubilized by water to disrupt the walls.

A visualization of the particles of this invention can be derived from U.S. Pat. No. 3,888,689, supra. FIGS. 1 and 2. FIG. 1 is representative of the particle structure, which has a large central core and a relatively thin wall. That thin wall, however, has a structure like the particle of FIG. 2 with small droplets/particles incorporated in the wall.

DETAILED DESCRIPTION OF THE INVENTION

The powdered abrasive cleanser composition contains from about 0.02% to about 5%, preferably from about 0.05% to about 2%, more preferably from about 0.1% to about 0.5% of microencapsulated perfume. The preferred wall materials in said microcapsules are those typically used to form microcapsules by coacervation techniques. The materials are described in detail in the following patents incorporated herein by reference, e.g., U.S. Pat. Nos. 2,800,458; 3,159,585; 3,533,958; 3,697,437; 3,888,689; 3,996,156; 3,965,033; 4,010,038; and 4,016,098. The preferred encapsulating material is gelatin coacervated with a polyanion such as gum arabic and cross-linked with a cross-linking material such as glutaraldehyde. The amount of cross-linking agent used in these microcapsules is preferably equivalent to from about 4% to about 20%, preferably from about 6% to about 18%, more preferably from about 8% to about 10%, even more preferably from about 10% to about 14% glutaraldehyde based on the gelatin.

The microcapsule walls herein preferably contain smaller wall inclusion "particles" (includes liquid droplets) having diameters that are no more than about 25%, preferably less than about 15%, more preferably less than about 10%, of the diameter of the central core portion of the microcapsule described hereinafter. Even more preferably, these inclusion particles have diameters that are from about 0.1% to about 10% of the central core's diameter.

The preferred smaller wall inclusion "particles" in the walls of the preferred microcapsules are preferably materials which can be activated, e.g., by water, etc. They can be either solids or liquids. If the wall is somewhat porous and the small wall inclusion particles are water-soluble, the water-soluble wall particles can be dissolved and removed to create a porous wall structure that will permit the hydrophobic core material to escape.

The central core portions of the microcapsules are relatively large. The core portion should be at least about 50 microns in diameter, preferably from about 50 to about 350 microns, more preferably from about 75 to about 300 microns, and even more preferably from about 100 to about 250 microns in diameter. As pointed out in U.S. Pat. No. 3,888,689, supra, such microcapsules are very efficient, since a relatively large amount of core material is surrounded by a relatively small amount of wall material. At least about 50% preferably at least about 60%, and: more preferably at least about 75% of the microcapsules are within the stated ranges.

The thinnest part of the wall around the central core in any microcapsule can vary from about 0 5 to about 50 microns, preferably from about 5 to about 25 microns In complex microcapsules, the thinnest part of the wall is preferably at least about 2 microns.

The Core Material

Perfume ingredients useful herein are disclosed in U.S. Pat. Nos. 4,515,705, supra, and 4,714,856, supra. Encapsulated perfumes are extremely desirable for use in the powdered abrasive cleanser compositions of this invention. Encapsulated perfumes are more likely to survive during storage, especially in the presence of bleach materials.

It is a specific and unique advantage of encapsulated materials such as perfumes that more volatile components can be delivered to the cleaning process. Such volatile perfume ingredients, can be defined in a preferred way as having a vapor pressure greater than about 3 microns of mercury at 25° C. up to and including materials having vapor pressures of about 5,000 microns of mercury. Components having vapor pressures that are less than about 3 microns of mercury at 25° C. can also be delivered more effectively by microencapsulation, as set forth herein, than by simple incorporation. Such materials can include materials such as perfume ingredients classified as middle and top notes, which are sometimes desirable since many such notes can be used to convey an improved freshness impression. In a preferred aspect of the invention, only a portion of the perfume is encapsulated.

In general, there are two types of perfume ingredients that are sometimes desirably included in perfume compositions that are encapsulated, especially coacervate microcapsules, and more especially coacervate microcapsules having a complex structure, for use in hard surface abrasive cleansers. Ingredients with good water solubility and small amounts of surface active ingredients are acceptable and can even be desirable for improved release. However, using a slightly more hydrophobic perfume appears to provide more consistent microcapsule structures, especially those with a complex structure.

Also, it may, or may not, be desirable to encapsulate very high boiling materials, e.g., those having boiling points in excess of about 300° C., in the microcapsules. Such materials lower the volatility of the total perfume so that they provide a benefit if the perfume composition is too volatile. However, if the perfume's volatility is already too low, they reduce the ability of the perfume to provide the desired effect during use.

The Wall Material

The materials used to form the wall are typically, and preferably, those used to form microcapsules by coacervation techniques. The materials are described in detail in the patents incorporated hereinbefore by reference, e.g., U.S. Pat. Nos. 2,800,458; 3,159,585; 3,533,958; 3,697,437; 3,888,689; 3,996,156; 3,965,033; 4,010,038; and 4,016,098.

The preferred encapsulating material for perfumes is gelatin coacervated with a polyanion such as gum arabic and, preferably, cross-linked with glutaraldehyde. The preferred gelatin is Type A (acid precursor), preferably having a bloom strength of at least about 300 or, less preferably, 275, then by increments of 25, down to the least preferred 150. A spray dried grade of gum arabic is preferred for purity. Although gelatin is always preferred, other polyanionic materials can be used in place of the gum arabic. Polyphosphates, alginates (preferably hydrolyzed), carrageenan, carboxymethylcellulose, polyacrylates, silicates, pectin, Type B gelatin (at a pH where it is anionic), and mixtures thereof, can be used to replace the gum arabic, either in whole or in part, as the polyanionic material.

Other preferred parameters, in addition to suitable agitation to produce a bimodal distribution, include: (1) The use of from about 5 to about 25, preferably from about 6 to about 15, more preferably from about 7 to about 12, and even more preferably from about 8 to about 10, grams of gelatin per 100 grams of perfume (or other suitable material) that is encapsulated (2) The use of from about 0.4 to about 2.2, preferably from about 0.6 to about 1.5, more preferably from about 0 8 to about 1.2, grams of gum arabic (or an amount of another suitable polyanion to provide an approximately equivalent charge) per gram of gelatin. (3) A coacervation pH of from about 2.5 to about 8, preferably from about 3.5 to about 6, more preferably from about 4.2 to about 5, and even more preferably from about 4 4 to about 4.8. (The pH range is adjusted to provide a reasonable balance between cationic charges on the gelatin and anionic charges on the polyanion.) (4) Effecting the coacervation reaction in an amount of deionized water that is typically from about 15 to about 35, preferably from about 20 to about 30, times the amount of the total amount of gelatin and polyanionic material used to form the capsule walls. Deionized water is highly desirable for consistency since the coacervation reaction is ionic is nature (5) Using a coacervation temperature between about 30° C. and about 60° C., preferably between about 45° C. and about 55° C. (6) After the desired coacervation temperature is reached, using a cooling rate of from about 0.1° C. to about 5° C., preferably from about 0.25° C. to about 2° C. per minute. The cooling rate is adjusted to maximize the time when the coacervate gel walls are being formed. For example, polyphosphate anions form coacervates that gel at higher temperatures, so the cooling rate should be kept slow at first and then speeded up. Gum arabic forms coacervates that gel at lower temperatures, so the cooling rate should be fast at first and then slow.

The gelatin/polyanion (preferably gum arabic) wall is preferably cross-linked. The preferred cross-linking material is glutaraldehyde. Suitable parameters, in addition to suitable agitation, for cross-linking with glutaraldehyde are: (1) The use of from about 0.05 to about 2.0, preferably from about 0.5 to about 1, grams of glutaraldehyde per 10 grams of gelatin. (2) Cooling the microcapsule slurry to a temperature of less than about 10° C. and letting it remain there for at least about 30 minutes before adding the glutaraldehyde. The slurry is then allowed to rewarm to ambient temperature. (3) Keeping the pH below about 5.5 if the cross-linking reaction is over about 4 hours in length. (Higher pH's and/or temperatures can be used to shorten the reaction time.) (4) Excess glutaraldehyde is removed to avoid excessive cross-linking by washing with an excess of water, e.g., about 16 times the volume of the capsule slurry. Other cross-linking agents such as urea/formaldehyde resins, tannin materials such as tannic acid, and mixtures thereof can be used to replace the glutaraldehyde either in whole or in part.

In addition to the coacervation encapsulates, other microencapsulation processes can be used including those described in U.S. Pat. No. 4,269,727, supra; U.S. Pat. No. 4,303,548, supra; and U.S. Pat. No. 4,460,722, supra, all of said patents being incorporated herein by reference, to prepare the preferred complex structure where the wall contains small "particles" that can weaken the wall and thus promote release.

The complex wall structures will typically contain from about 1% to about 25%, preferably from about 3% to about 20%, more preferably from about 5% to about 15%, and even more preferably from about 7% to about 13%, of the weight of the core material of wall inclusion material having particle sizes as set forth hereinbefore. The particles included in the wall can be either the central core material or can be different. Compounds that dissolve when exposed to water, e.g., can be used. The goal is to have a very strong wall during processing and storage and then to decrease the strength of the wall at a desired time and thus allow the core material to escape, either all at once, or slowly, by passing through the resultant more porous wall structure. This complex wall structure is very important since the primary mechanism for destroying the wall is mechanical action. The wall material is water-insoluble to provide maximum processing strength. It is therefore surprising that the mechanical action during use provides acceptable release.

The abrasive cleansers described herein contain from about 0.1% to about 10%, preferably from about 1% to about 6%, of suitable surfactant. The water-soluble organic detergent surfactants which can be used in the detergent compositions of this invention are the anionic, nonionic, zwitterionic and cationic organic detergents. Some examples of such well-known surfactants are disclosed in U.S. Pat. Nos. 3,583,922; 3,829,385; 3,715,314; and 4,287,080, supra, the foregoing patents being incorporated herein by reference.

Particularly preferred detergent compounds for use in the present powdered abrasive cleansers are the non-soap anionic detergents, particularly the alkyl benzene sulfonate detergents wherein the alkyl group has from about 8 to about 18 carbon atoms. Suitable examples are sodium decyl benzene sulfonate, sodium dodecyl and pentadecyl sulfonates wherein the dodecyl and pentadecyl groups are derived from a propylene polymer, and sodium octadecyl benzene sulfonates. Other preferred anionic detergents are the surface active sulfated or sulfonated aliphatic compounds, preferably having from about 8 to about 22 carbon atoms. Examples thereof are the long chain pure or mixed higher alkyl sulfates, e.g., lauryl sulfates and coconut fatty alcohol sulfates and the $C_{12}$–$C_{18}$ paraffin sulfonates. The anionic detergent components are commonly used in the form of their water-soluble salts. Preferred water-soluble cations are the alkali metal and ammonium cations, the sodium and potassium cations being particularly preferred.

The powdered abrasive cleansers of the present invention contain from about 10% to about 95%, preferably from about 40% to about 90%, more preferably from about 60% to about 85%, of water-insoluble abrasive material. The preferred abrasive materials for use herein are silica, calcium carbonate, feldspar, and mixtures thereof. The abrasive particles should have a diameter of from about 0.3 millimeters to about 0.001 millimeters or finer. Other abrasive materials are disclosed by example in U S Pat. Nos. 3,583,922; 3,829,385; 3,715,314; and 4,287,080, supra, the foregoing patents being incorporated herein by reference.

The powdered abrasive cleansers of the present invention contain from about 0% to about 80%, preferably from about 5% to about 20%, detergency builder. Detergency builders are employed for enhanced cleaning effects. They enhance the detergency effect of the organic detergent component by sequestration or precipitation of hardness ions and/or by providing alkalinity. Suitable detergency builders include highly alkaline materials such as sodium sesquicarbonate, trisodium phosphate, sodium pyrophosphate, sodium tripolyphosphate, sodium dibasic phosphate, and sodium hexametaphosphate, sodium silicates having a silicon dioxide to disodium oxide ratio of 1:1 to 3.2:1, sodium carbonate, and borax. Other detergency builders include organic materials such as sodium citrate and trisodium nitrilotriacetate. Mixtures of two or more inorgance or organic can be employed. Other examples of suitable detergency builders include those described in U.S. Pat. No. 3,309,319, at Col. 4, line 44 through Col. 5, line 9, the patent being incorporated herein by reference.

The cleanser compositions of the present invention can also contain from about 0.5% to, depending on the detergency builder used, about 10% moisture, preferably less than about 5%.

The abrasive cleansers of this invention can, and preferably do, contain oxidizing agent for bleaching.

The common oxidizing materials used with abrasive cleansers are present such that the bleach active is at a level of from about 0.1% to about 5%. Examples are potassium and sodium dichloroisocyanurates and chlorinated trisodium phosphate. Other oxidizing bleaches for use in the solid abrasive cleansers of the present invention are disclosed in U.S. Pat. Nos.: 3,583,922; 3,829,385; 3,715,314; and 4,287,080, supra, the foregoing patents being incorporated herein by reference.

Other ingredients which can also be present in the powdered abrasive cleansers of the present invention include inorganic salts such as sodium chloride, sodium sulfate, potassium chloride, and potassium sulfate, these being included in the composition in amounts less than about 20% by weight of the composition. Sodium acetate may be added to the composition as a stabilizing compound for the oxidizing bleach, at a level of about 2–10 times the amount of free or loosely bound moisture which is encountered in the compositions during processing or as a result of humidity. Other minor ingredients which can be included are anticaking agents such as hydrated magnesium trisilicate or sodium carboxymethyl cellulose, sulfamic acid, perfume, antiseptics, germicides, aluminium mark removing agents such as calcium oxide or hydroxide, coloring agents, and the like.

All percentages, ratios and parts, herein are by weight unless otherwise stated.

EXAMPLE

Making Complex Microcapsules

Complex microcapsules are prepared according to the following generic process. Details on the individual microcapsules are contained in Table 1.

The indicated amounts of gelatin with the indicated Bloom strengths are dissolved into the indicated amounts of deionized water having the indicated temperatures in 800 ml beakers that serve as the main reaction vessels.

The indicated amounts of spray dried gum arabic are dissolved into the indicated amounts of deionized water having the indicated temperatures.

For microcapsules 1–5, the indicated amounts of a conventional perfume composition (containing about 30% orange terpenes (90% d-limonene), 10% linalyl acetate, 20% para tertiary butyl cyclohexyl acetate, 30% alpha ionone, and 10% para tertiary butyl alpha methyl hydrocinnamic aldehyde) which is fairly volatile, are emulsified with a laboratory mixer equipped with a Lightnin R-100 impeller into the gelatin solutions at high rpm (about 1600) such that after about 10 minutes the droplet size of the perfume is between about and about 10 microns This is the "fine emulsion."

The indicated amounts of the same perfume containing d-limonene are emulsified into the previously formed "fine emulsion" using the same mixer with a Lightnin A-310 impeller set at a lower rpm (about 350) such that after about 10 minutes a new, second, size distribution of perfume emulsion "particles" with a mean size of about 175 microns (coarse emulsion) are produced The "fine emulsion" is still present. In microcapsules 6 and 7, the same process is used, but the perfume contains about 11.1% of ethyl amyl ketone; ionone alpha; ionone beta; ionone gamma methyl; ionone methyl; iso jasmone; iso menthone; and methyl beta-napthyl ketone and 11.2% of methyl cedrylone and the perfume is encapsulated with 30% dodecane.

The mixer is slowed to about 200 rpm.

The gum arabic solution is added and the indicated amounts of extra dilution deionized water at the indicated temperatures are added.

The pH is controlled as indicated. These pH's are selected by observing the pH at which the coacervates start forming. The solution/emulsions are cooled to room temperature in the indicated times The solution/emulsions are then cooled to the indicated temperatures and allowed to stand for about 30 minutes. The coacervate is then cross-linked with the indicated amounts of a 25% solution of glutaraldehyde. The cross-linking reaction takes the indicated times during which slow increase to ambient temperature occurs.

TABLE 1

| Microcapsules | 1 | 2 | 3 |
|---|---|---|---|
| Gelatin (gms) | 15 | 8 | 12 |
| Bloom Strength | 225 | 275 | 275 |
| Water (gms) | 150 | 100 | 100 |
| Temperature (°C.) | 50 | 50 | 50 |
| Gum Arabic (gms) | 10 | 8 | 8 |
| Water (gms) | 250 | 250 | 200 |
| Temperature (°C.) | 40 | 45 | 45 |
| Total Perfume (gms) | 125 | 100 | 100 |
| Fine Emulsion (gms) | 25 | 10 | 15 |
| Coarse Emulsion (gms) | 100 | 90 | 85 |
| Dilution Water (gms) | 150 | 150 | 250 |
| Temperature (°C.) | 50 | 50 | 50 |
| Approx. pH range | 4.5–4.7 | 4.6–4.8 | 4.6–4.8 |
| Cooling time to room temperature (hours) | ~1 | ~1 | ~2 |
| Initial cross-linking temperature (°C.) | 15 | 10 | 20 |
| Glutaraldehyde (gms of 25% solution) | 12 | 4 | 4 |
| Cross-linking time (hours) | 15 | 15 | 24 |

| Microcapsules | 4 | 5 | 6 |
|---|---|---|---|
| Gelatin (gms) | 10 | 10 | 8 |
| Bloom Strength | 250 | 300 | 300 |
| Water (gms) | 125 | 100 | 100 |
| Temperature (°C.) | 40 | 45 | 45 |
| Gum Arabic (gms) | 10 | 10 | 6 |
| Water (gms) | 250 | 250 | 225 |
| Temperature (°C.) | 40 | 45 | 45 |
| Total Perfume (gms) | 100 | 100 | 100 |
| Fine Emulsion (gms) | 15 | 10 | 5 |
| Coarse Emulsion (gms) | 85 | 90 | 95 |
| Dilution Water (gms) | 250 | 150 | 100 |
| Temperature (°C.) | 50 | 50 | 40 |
| Approx. pH range | 4.7–4.9 | 4.7–4.9 | 4.6–4.8 |
| Cooling time to room temperature (hours) | ~2 | ~2 | ~1 |
| Initial cross-linking temperature (°C.) | 20 | 5 | 15 |
| Glutaraldehyde (gms of 25% solution) | 5 | 4 | 6 |
| Cross-linking time (hours) | 24 | 16 | 4 |

TABLE 2

| Component | Wt. % |
|---|---|
| Compostion | |
| Calcium Carbonate (0.1-$\mu$200 particle size) | 70.0 |
| Chlorinated Trisodium Phosphate | 17.3 |
| Tetrasodium Pyrophosphate | 6.1 |
| LAS ($C_{12}$ benzene sulfonate) | 2.2 |
| Minors (dye, etc.) | 0.5 |
| Water | 3.9 |
| The resultant composition is: | |
| Final Composition | |
| Calcium Carbonate | 6.0 |
| Chlorinated Trisodium Phosphate | 13.8 |
| Syloid Silica 244FP | 10.0 |
| Tetrasodium Pyrophosphate | 4.9 |
| LAS ($C_{12}$ benzene sulfonate) | 1.8 |
| Minors (dye, etc.) | 0.4 |
| Encapsulated Perfume* | 0.15 |
| Water | 3.1 |

*The perfume is any of Microcapsules 1-6 described hereinbefore.

An excellent bleach-free powdered cleanser can be made by substituting trisodium phosphate (TSP) for the chlorinated TSP in the above formulation.

What is claimed is:

1. A powdered abrasive cleanser comprising:

(a) from about 0.1% to about 10% by weight surfactant;

(b) from about 10% to about 95% by weight water-insoluble abrasive material;

(c) from 0% to about 80% by weight detergency builder; and (d) from about 0.02% to about 5% perfume by weight contained in water-insoluble microcapsules prepared by a coacervation process between gelatin and polyanionic material selected from the group consisting of: (a) polyphosphates; (b) alginates; (c) carrageenan; (d) carboxymethyl cellulose; (e) polyacrylates; (f) gum arabic; (g) silicates; (h) pectin; (i) Type B gelatin; and (j) mixtures thereof, the walls of said microcapsules containing from about 1% to about 25%, by weight of the core material, of particles that have diameters of less than about 15 microns.

2. The cleanser of claim 1, wherein said microcapsules have been crosslinked with from about 4% to about 20% glutaraldehyde based on weight of gelatin.

3. The cleanser of claim 2 wherein the polyanionic material is gum arabic and the level of said glutaraldehyde is from about 6% to about 18%.

4. The cleanser of claim 3 wherein the level of said glutaraldehyde is from about 8% to about 18% and the level of perfume is from about 0.05% to about 2%.

5. The cleanser of claim 2 wherein the level of said glutaraldehyde is from about 8% to about 18% and the level of perfume is from about 0.05% to about 2%.

6. The cleanser of claim 2 wherein the level of perfume is from about 0.05% to about 2%.

7. The cleanser of claim 6 wherein the level of perfume is from about 0.1% to about 0.5%.

8. The cleanser of claim 2 containing from about 40% to about 90% abrasive and from about 1% to about 6% detergent.

* * * * *